United States Patent
Iannuzzi

(10) Patent No.: US 12,031,172 B2
(45) Date of Patent: Jul. 9, 2024

(54) METHOD FOR THE PREPARATION OF POLYHYDROXYBUTYRATE

(71) Applicant: ACBC S.r.l., Milan (IT)

(72) Inventor: Edoardo Iannuzzi, Milan (IT)

(73) Assignee: ACBC S.R.L., Milan (IT)

( * ) Notice: Subject to any disclaimer, the term of this patent is extended or adjusted under 35 U.S.C. 154(b) by 0 days.

(21) Appl. No.: 18/046,561

(22) Filed: Oct. 14, 2022

(65) Prior Publication Data

US 2023/0119428 A1      Apr. 20, 2023

(30) Foreign Application Priority Data

Oct. 15, 2021   (IT) .................. 102021000026486

(51) Int. Cl.
| | |
|---|---|
| *C12P 7/62* | (2022.01) |
| *C08G 63/89* | (2006.01) |
| *C12N 1/20* | (2006.01) |
| *C08G 63/06* | (2006.01) |
| *C12R 1/11* | (2006.01) |

(52) U.S. Cl.
CPC ............. *C12P 7/62* (2013.01); *C08G 63/89* (2013.01); *C12N 1/205* (2021.05); *C08G 63/06* (2013.01); *C12R 2001/11* (2021.05)

(58) Field of Classification Search
CPC  C12P 7/62; C08G 63/89; C08G 63/06; C12N 1/205; C12R 2001/11
See application file for complete search history.

(56) References Cited

U.S. PATENT DOCUMENTS

| | | | |
|---|---|---|---|
| 2003/0027293 A1 | 2/2003 | Bordoloi et al. | |
| 2012/0135480 A1* | 5/2012 | Nakas ................. | C12P 7/625 435/146 |
| 2017/0267577 A1 | 9/2017 | Wang et al. | |
| 2021/0332395 A1* | 10/2021 | Herrema ............... | C12P 7/62 |

FOREIGN PATENT DOCUMENTS

| | | |
|---|---|---|
| BR | 102015027786 A2 * | 5/2017 |
| IT | UA20161759 A1 | 9/2017 |

OTHER PUBLICATIONS

Dietrich K, Dumont MJ, Del Rio LF, Orsat V. Sustainable PHA production in integrated lignocellulose biorefineries. N Biotechnol. Mar. 25, 2019;49:161-168. doi: 10.1016/j.nbt.2018.11.004. Epub Nov. 19, 2018. PMID: 30465907. (Year: 2018).*
Wang J, Liu S, Huang J, Qu Z. A review on polyhydroxyalkanoate production from agricultural waste Biomass: Development, Advances, circular Approach, and challenges. Bioresour Technol. Dec. 2021;342:126008. doi: 10.1016/j.biortech.2021.126008. Epub Sep. 22, 2021. PMID: 34592618. (Year: 2021).*
Hassan et al., Internat. J. Enviro. Technol., 16:3497-3512 (2019) (Year: 2019).*
Muniyandi et al., BEPLS, 10(10):86-94 (2021) (Year: 2021).*
Pandian et al., Biosource Technol., 101:705-711 (2010) (Year: 2010).*
Paul et al., Internat. J. ChemTech Res., 10(7):884-904 (2017) (Year: 2017).*
Sathiyanarayanan et al., Internat. J. Biol. Macromol., 59:170-177 (2013) (Year: 2013).*
Dimou et al., "Wine lees valorization: Biorefinery development including production of a generic fermentation feedstock employed for poly(3-hydroxybutyrate) synthesis", Food Research International, 2015, vol. 73, pp. 81-87.
Kusaka et al., "Molecular mass of poly[(R)-3-hydroxybutyric acid] produced in a recombinant *Escherichia coli*", Applied Microbiology and Biotechnology, 1997,vol. 47 pp. 140-143.
Italian Search Report for Corresponding Italian Application No. 202100026486, Jun. 4, 2022, 15 pages.

* cited by examiner

*Primary Examiner* — Thomas J. Visone
(74) *Attorney, Agent, or Firm* — Lucas & Mercanti, LLP

(57) ABSTRACT

The present invention relates to methods for the preparation of high molecular weight polyhydroxybutyrate (PHB) by culturing *Bacillus megaterium* strains in a mixture of agri-food wastes, PHB obtained or obtainable by the methods as well as to its use in the preparation of articles such as, for example, soles and/or heels for shoes.

4 Claims, No Drawings

METHOD FOR THE PREPARATION OF POLYHYDROXYBUTYRATE

CROSS-REFERENCE TO RELATED APPLICATIONS

This application claims the benefit of priority from Italian Patent Application Number 102021000026486 filed on Oct. 15, 2021, the contents of which are incorporated herein by reference.

FIELD OF THE INVENTION

The present invention relates to methods for the preparation of bioplastics, in particular polyhydroxybutyrate, by culturing bacterial strains in a mixture of agri-food wastes as well as to its use in the preparation of articles such as, for example, soles and/or heels for footwear.

BACKGROUND OF THE INVENTION

In the last decades several studies have been carried out to try to reduce the environmental impact of synthetic plastics (PET, PVC, PP, PE). Despite this, the problem of the disposal of plastics, also considering their vast use, still remains an important environmental and socio-economic problem. Consequently, research has focused on the development of "bioplastics" or plastics obtained from renewable sources (for example, cellulose, starch, lactic acid) which, in general, are biodegradable.

Also belonging to the category of bioplastics are materials obtained from a biomass capable of synthesizing polymer chains as intermediate products of their own metabolism. For example, polyhydroxyalkanoates, a class of linear polyesters, are produced by different strains of gram-negative and gram-positive bacteria. The bacterial biosynthesis of polyhydroxyalkanoates begins with the condensation of two molecules of acetyl-CoA to give acetoacetyl-CoA which is subsequently reduced to hydroxybutyryl-CoA. The latter compound is the monomer that polymerizes to give poly-β-hydroxybutyrate. Poly-β-hydroxybutyrate is stored inside cells in the form of granules, which can reach up to 90% of the dry weight of the bacterial mass.

It is known that the substrate used for the biosynthesis, the nutrients supplied to the bacterial cells and the culture conditions can influence the production of polyhydroxyalkanoates both in terms of yield and of the type of polymer obtained. Among the polyhydroxyalkanoates, the most advantageous is certainly polyhydroxybutyrate as it has physical properties similar to polypropylene. It is insoluble in water, has good oxygen permeability, good resistance to ultraviolet rays and is biocompatible.

However, to date, the applications of this polymer are severely limited by its limits in mechanical properties such as elastic modulus, elongation at break, serrated impact force and by the costly and time-consuming process for its preparation. The substrates selected are very expensive, the growth phase may require long processing times and/or sterile conditions, the yield of the process is often very low, the recovery and purification operations of the polyhydroxybutyrate require specific equipment, etc. In addition, the processes known in the art do not always guarantee obtaining a bioplastic having the characteristics or the performances suitable for the desired field of application.

Therefore, there is still a need for processes for the production of polyhydroxybutyrate which overcome the disadvantages of those already known in the art.

SUMMARY OF THE INVENTION

Since some of the main disadvantages of the production of polyhydroxybutyrate or poly-β-hydroxybutyrate (hereinafter, for the sake of brevity, also PHB) on an industrial scale include poor mechanical properties and high processing costs, the present invention includes methods for the preparation of PHB based on the recycling of waste substances while at the same time improving the mechanical properties of the PHB. In fact, the present invention refers to the research and identification of mixtures based on agri-food wastes suitable to act as nourishment for bacterial cells that are able to produce PHB under particular culture conditions.

Without wishing to be bound by any theory, it is noted that by using a mixture of agri-food wastes, better defined below, the bacterial cells produce polyhydroxybutyrate in a reproducible and effective manner.

The present invention therefore includes a method for the preparation of polyhydroxybutyrate or a salt thereof which comprises the following steps:
  incubating one or more bacterial strains in a culture medium comprising, or consisting of, a mixture of agri-food wastes, said one or more bacterial strains, producing polyhydroxybutyrate; and
  separating and/or collecting the polyhydroxybutyrate thus obtained from the culture medium.

The agri-food wastes mixture, better defined hereinafter, represents a further aspect of the present invention as well as the use of said mixture as (co)adjuvant in the preparation of polyhydroxybutyrate. It has in fact been noted that bacterial strains, in particular belonging to the *Bacillus genus*, when cultivated in the presence of the agri-food wastes mixture of the present invention synthesize and accumulate PHB in an effective way.

Furthermore, by using a culture medium comprising, or consisting of, said agri-food wastes mixture, the bacterial cells produce a high molecular weight polyhydroxybutyrate. The PHB obtainable by the method of the invention has improved physical and mechanical properties which make it particularly suitable for the replacement of plastic materials.

Therefore, the invention also refers to polyhydroxybutyrate obtained or obtainable by means of the method of the present invention, as well as to articles which include the PHB, such as, for example, soles and/or heels for footwear, as well as to methods for the preparation thereof.

The inventor has therefore found that the use of a mixture of wastes, in particular agri-food wastes, as a substrate for the culture of bacterial cells capable of producing PHB, provides a valid solution to the problem of waste disposal and, at the same time, responds to the need for an improved process for the preparation of PHB which is more advantageous, or at least an alternative to those processes known in the art.

Procedures for the production of PHB have been described in the art which provide for the incubation of a bacterial strain in a culture medium comprising various types of vegetable substances, even as wastes (see, for example, PCT international patent application published as WO2009/149525, Italian patent application no.102016000028033, US patent publication US 2003/027293 A1 or Dimou, C. et al. *I Food Research International,* 73 (2015) 81-87). All of the foregoing are in agreement that the biomass used as food for bacteria must have very specific characteristics in order to be effectively used in the production of PHB, in particular nutritional characteristics suitable for the specific microorganism to be cultivated.

Advantageously, the polyhydroxybutyrate obtained according to the method of the present invention has a high molecular weight and physical characteristics which make it particularly suitable for making articles such as soles and/or heels for footwear.

Further features and advantages of the invention will become apparent from the following detailed description and examples.

Glossary

The terms used in the present description are as generally understood by the person skilled in the art, unless otherwise indicated.

In the context of this description, "compounding" of plastic materials means the process of preparing formulations and compounds by dissolving and mixing in a dispersive and distributive way molten polymers, additives and/or fillers. In order to obtain a homogeneous mixture from the different raw materials, twin screw extruders are used. These extrusion systems allow both mixing and extrusion to be carried out in a single step. More precisely: by compounding, thermoplastic polymers (for example in the form of granules, powders, grits, etc. together with additives, powder fillers, aggregates, etc.) are melted and mixed; the discharged melt stream is cooled and granulated into a plastic material ready for molding.

The term "comprising", in the context of this disclosure, also means "consisting essentially of" or "consisting of".

In the context of this disclosure, "about" refers to the experimental error that may occur during conventional measurements. More specifically, when it refers to a value, it indicates ±5% of the indicated value and when it refers to an interval ±5% of the extremes thereof.

DETAILED DESCRIPTION OF THE INVENTION

As mentioned above, recently polyhydroxyalkanoates and in particular polyhydroxybutyrate have been the subject of various studies. Also, thanks to their thermoplastic properties, they represent promising alternatives to plastics of fossil origin. However, the use of these bioplastics on an industrial level is limited by the high costs of treatment and transformation of the raw materials needed for their production. The use of waste materials or wastes as a raw material for the production of PHB could therefore represent a useful solution to make this technology available on the market. At the same time, using resources traditionally known as mere waste materials, the principles of circular economy are respected, making the preparation process of these bioplastics even more eco-sustainable.

An object of this invention is therefore to identify renewable materials, for example obtained from wastes, which can be used as a culture medium and/or nourishment, in particular, as a source of carbon, in the biosynthesis of PHB by particular bacterial cultures.

Therefore, the present invention refers to a method for the preparation of polyhydroxybutyrate or a salt thereof which comprises the following steps:

incubating one or more bacterial strains in a culture medium comprising a mixture of agri-food wastes, said one or more bacterial strains, producing polyhydroxybutyrate; and separating the polyhydroxybutyrate thus obtained from the culture medium.

The bacterial strains mentioned above can be selected from bacteria capable of accumulating polyhydroxybutyrate as an intermediate product of their cellular metabolism. By way of non-limiting example, said one or more bacterial strains are strains belonging to the genus *Bacillus*, can preferably be selected from the group comprising, or consisting of: *Bacillus megaterium, Bacillus Subtilis, Bacillus mycoides* and mixtures thereof. More preferably, the bacterial strain is *Bacillus megatarium*, and still more preferably, the strain is *Bacillus megatarium* QM B1551.

Generally, the bacterial strains are cultured in a continuous fermenter (for example CSTR: continuously stirred tank reactor), preferably with a pH of 7.0 or about 7.0 and a temperature of 30° C. or about 30° C. for 10 hours or about 10 hours. In this bioreactor it is possible to ascertain, at the same time and independently, various process parameters such as voltage, pH, dissolved oxygen (OD) and $CO_2$ accumulation, thus causing a greater speed of growth and population density.

Preferably, for *Bacillus megatarium* QM B1551 the incubation phase includes two sub-phases: first the production of biomass in CSTR and then in a batch reactor in which the incubation conditions are adjusted in favor of the carbon source, preferably maintaining a pH of 7.0 and a temperature of 35° C. for 48 hours. Although not strictly necessary, it has been noted that this combination of sub-steps improves the productivity and synthesis quality of the biopolymer.

The integration of wastes in the culture medium of the present invention contributes to further reducing the costs associated with the processes for the production of PHB since no ad hoc culture substrates must be used. At the same time, the addition of wastes in the culture medium of the present invention reduces the environmental impact since waste materials are used which, if not used as described herein, should be disposed of in a specific way.

The mixture of wastes referred to in the present invention can include all types of wastes identified with the code CER 02 (Waste produced from agriculture, horticulture, forestry, hunting and fishing, preparation and processing of food) referred to in the European List of Waste (EER) which is incorporated herein its entirety by reference.

However, it has been found that a mixture of agri-food wastes comprising, or consisting of, orange peels, wheat bran, rice husks, olive oil vegetable water and/or pomace or mixtures thereof, is particularly advantageous for purpose of the present invention.

Therefore, the invention relates to a method for the preparation of polyhydroxybutyrate, according to any of the embodiments herein described, which includes the following steps:

incubating one or more bacterial strains in a culture medium comprising a mixture of agri-food wastes, one or more bacterial strains, producing polyhydroxybutyrate; and separating and/or collecting the polyhydroxybutyrate thus obtained from the culture medium wherein the mixture of agri-food wastes comprises solid agri-food wastes which are preferably selected from orange peels, wheat bran, rice husks and mixtures thereof and/or liquid agri-food wastes which are preferably selected from olive oil vegetation waters, pomace and mixtures thereof.

According to any one of the embodiments described herein, the agri-food waste mixture comprises, or consists of, orange peels, wheat bran, rice husks and olive oil vegetation waters and/or pomace.

According to an embodiment, the agri-food waste mixture comprises, or consists of, orange peel, wheat bran, rice husk and olive oil vegetation water and/or pomace as the only agri-food wastes. In other words, according to this last embodiment, the mixture may comprise other components, for example additives and excipients, provided that these do not belong to the class of agri-food wastes as identified above.

By way of example, the agri-food waste mixture according to an embodiment of the present invention does not include at least one, at least two, at least three, at least four, at least five or more of the following: apple, apple bagasse or its derivatives, pineapple waste, molasses, common reed (*Arundo donax L.*), wine lees or fragments of grape skins and seeds, inverted sugars, hydrolyzed starch derived from the processing of potatoes, etc; ingredients that can lead to a lower process yield or in any case to obtain a PHB with characteristics different from those desired, for example in terms of molecular weight of the PHB obtained.

In any case, it has been noted that by using as nourishment a mixture comprising at least orange peels, wheat bran, rice husks (or at least the soluble fraction thereof) together with olive oil vegetation water and pomace, the bacterial cells they accumulate PHB very effectively.

Therefore, the present invention also refers to a culture medium for the cultivation of one or more bacterial strains, preferably of *Bacillus megatarium*, comprising, or consisting of, a mixture of solid and liquid agri-food wastes wherein said solid agri-food wastes comprises orange peels, wheat bran, rice husks or mixtures thereof and wherein said liquid agri-food wastes comprise olive oil vegetation water, pomace or mixtures thereof. The agri-food waste mixture and/or the culture medium can further comprise suitable additives as better specified below.

In the context of the present invention, suitable additives can be additives generally known in the art to be suitable for culture media with particular reference to *Bacillus megatarium*. For example, said additives are preferably selected from the group comprising, or consisting of, natural plasticizing agents such as derivatives of vegetable oils. Vegetable oil derivatives can be, for example, selected from the group comprising, or consisting of, epoxidized castor oil triglycerides, epoxidized soybean oil, cardanol oil, epoxidized linseed oil and mixtures thereof. The plasticizers are advantageous for an improvement of the mechanical properties as they induce a lower viscosity of the mixture and improve the elastic modulus.

In a preferred embodiment, the mixture comprises orange peels, wheat bran, rice husks, olive oil vegetable water and pomace together with at least one additive selected from the group comprising, or consisting of, epoxidized triglycerides of olive oil, castor oil, epoxidized soybean oil, cardanol oil, epoxidized linseed oil and mixtures thereof. For example, the mixture may comprise, or consist of: orange peels, wheat bran, rice husks, olive oil vegetation water and pomace and epoxidized triglycerides of castor oil.

Alternatively, the mixture may comprise, or consist of: orange peels, wheat bran, rice husks, olive oil vegetation water and pomace and soybean oil.

The quantity of each component in the mixture can be varied to adjust/modify the properties of the PHB polymer also depending on its intended use. However, in some aspects of the invention, the ingredients can be:
orange peel present in an amount of between 10-15% by weight of the total weight of the mixture; and/or
wheat bran present in an amount of between 5-10% by weight of the total weight of the mixture; and/or
rice husk present in an amount of between 5-10% by weight of the total weight of the mixture; and/or
olive oil vegetation waters and pomace are present in a quantity of between 60-65% by weight of the total weight of the mixture. The mixtures of agri-food wastes in the amounts above exert their beneficial effects in an optimal way ensuring an effective synthesis of PHB.

When present, the additives in the mixture can be present overall in an amount of between 1 and 3% by weight of the total weight of the mixture or, more generally, to the compensate the mixture up to 100%.

Without wishing to be bound to any theory, the inventor has surprisingly found that when said solid agri-food wastes is mixed with said liquid agri-food wastes in a weight ratio from about 20:80 to about 40:60, or preferably about 35:65 based on the total weight of the mixture, it allows an increase in the yield of the method (understood as % by weight of PHB on the weight of the dry cell mass) and/or to obtain a PHB with a high molecular weight particularly suitable for replacing plastic materials, in particular for use in the production of soles and/or heels for footwear.

Therefore, the present invention also refers to a method for the preparation of PHB or a salt thereof which comprises the following steps:
incubating one or more bacterial strains in a culture medium comprising an agri-food waste mixture, in which the agri-food waste mixture comprises solid agri-food wastes preferably selected from orange peels, wheat bran, rice husks and mixtures thereof and liquid agri-food wastes, preferably selected from olive oil vegetation waters, pomace and mixtures thereof; said one or more bacterial strains producing polyhydroxybutyrate;
separating and/or collecting the polyhydroxybutyrate thus obtained from the culture medium;
wherein the weight ratio between said solid agri-food wastes and said liquid agri-food wastes is between about 20:80 and about 40:60, preferably about 35:65 based on the total weight of the mixture.

Therefore, the present invention relates in particular to a method for the preparation of polyhydroxybutyrate (PHB) or a salt thereof comprising the following steps:
incubating one or more bacterial strains, preferably *Bacillus megatarium*, in a culture medium comprising a mixture of agri-food wastes, said one or more strains, producing polyhydroxybutyrate; and
separating and/or collecting the polyhydroxybutyrate from the culture medium,
wherein the agri-food waste mixture comprises solid agri-food wastes comprising (or consisting of) orange peel, wheat bran and rice husk and liquid agri-food wastes comprising (or consisting of) vegetation waters from olive oil and olive oil pomace, and
wherein said solid agri-food wastes (or a soluble fraction of said solid agri-food wastes, as better explained in the following) and liquid agri-food wastes are in a weight ratio from about 20:80 to about 40:60, and more preferably about 35:65 based on the total weight of the mixture.

The solid fraction of the agri-food wastes of the mixture can be previously pre-treated by heat with water, preferably with distilled water, to separate the insoluble fraction, which includes for example cellulose and lignin, from the soluble fraction which includes, for example, polysaccharides and then mix the soluble fraction thus obtained with liquid agri-food wastes to give a mixture of agri-food wastes. Optimal results have been obtained by using a mixture of agri-food wastes in which the weight ratio between the soluble fraction of said solid agri-food wastes and said liquid agri-food wastes is between about 20:80 and about 40:60, more preferably about 35:65 on the total weight of the mixture.

Therefore, the present invention also refers to a method for the preparation of polyhydroxybutyrate or a salt thereof which further comprises the steps of:

pretreating the solid agri-food wastes with a suitable solvent, preferably distilled water, so as to separate the soluble fraction of said solid agri-food wastes; and/or mixing the soluble fraction of said solid agri-food wastes thus obtained with the liquid agri-food wastes, preferably wherein the weight ratio between the soluble fraction of said solid agri-food wastes and said liquid agri-food wastes is between 20:80 and 40:60, more preferably 35:65 on the total weight of the mixture.

Furthermore, the present invention also refers to a method for the preparation of PHB or a salt thereof which comprises the following steps, in any order:

incubating one or more bacterial strains in a culture medium comprising an agri-food waste mixture, in which the agri-food waste mixture comprises solid agri-food wastes preferably selected from orange peel, wheat bran, rice husk and mixtures thereof and liquid agri-food wastes preferably selected from olive oil vegetation waters, pomace and mixtures thereof; said one or more bacterial strains producing polyhydroxybutyrate;

separating and/or collecting the polyhydroxybutyrate thus obtained from the culture medium;

pre-treating the solid agri-food wastes with a suitable solvent, preferably distilled water, to separate the soluble fraction of said solid agri-food wastes and mix the soluble fraction of said solid agri-food wastes thus obtained with the liquid agri-food wastes, wherein the weight ratio between said solid agri-food wastes (or the soluble fraction of said solid agri-food waste) and said liquid agri-food wastes is between 20:80 and 40:60, preferably 35:65 on the total weight of the mixture.

Once synthesized and stored in the cells, the PHB can be separated from the cell culture according to any of the methods known in the art, for example, by lysis of the bacterial cells and subsequent filtration of the culture medium.

According to any one of the embodiments of the method of the present invention, the recovery of the granules contained in the bacterial cells comprises the cell lysis followed by the separation of the biopolymer from the rest of the cellular materials. The direct extraction of PHA and, in particular PHB, from biomass is generally performed at room temperature preferably by means of halogenated solvents such as, by way of example but not limited to, chloroform, dichloromethane or 1,2-dichloroethane, and using an anti-solvent (ethanol, methanol or acetone) the solubility of the polymer can be reduced causing precipitation of the granules. The extraction takes place with immersion in distilled water (hypotonic medium) and causes the fragility of the cell wall, the cell swells and the wall is damaged by releasing the various components in the suspension medium. Due to their size and density, the PHA granules are recoverable after centrifugation, sedimentation or filtration.

The PHB can also be purified by means of a first washing with detergents such as, for example, sodium dodecyl sulfate (or SDS) and, optionally, a further washing, flocculation and finally drying. The polymer is obtained in the form of a white powder which can then be melted, extruded and converted into granules according to the traditional technology of petrochemical synthesis polymers. Therefore, the method of the present invention can also comprise one or more of the following steps, in any order or in any case not necessarily in this order:

Incubating *Bacillus megatarium* QM B1551 in a CSTR reactor with an agri-food waste mixture, wherein preferably the agri-food waste mixture comprises solid agri-food wastes such as orange peel, wheat bran, rice husk and liquid agri-food wastes such as olive oil vegetation water, pomace and optionally at least one plasticizer additive selected between epoxidized triglycerides of castor oil, epoxidized soybean oil, cardanol oil, epoxidized linseed oil or mixtures thereof;

Incubating *Bacillus megatarium* QM B1551 in a batch reactor wherein the incubation conditions are adjusted in favor of the carbon source, preferably wherein said incubation conditions are a pH of 7.0 and a temperature of 35° C. for 48 h.

Recovering the granules contained in the bacterial cells, by cell lysis, followed by the separation of the biopolymer from the rest of the cellular materials.

Extracting PHA, in particular PHB, from biomass at room temperature using halogenated solvents such as chloroform, dichloromethane, 1,2-dichloroethane or mixtures thereof, and optionally also an anti-solvent for example chosen from ethanol, methanol, acetone or mixtures thereof.

after immersing the PHA, in particular the PHB, in distilled water (hypotonic medium), centrifugating, sedimenting and filtering.

optionally washing the PHA, in particular PHB, with detergents such as, for example, SDS to purify the polymer.

optionally carry out a further washing, flocculation and drying.

The polymer is derived in the form of a white powder which is then melted, extruded and converted into granules according to the traditional technology of petrochemical synthesis polymers.

The above steps can be combined in various ways as immediately apparent to a person skilled in the art.

As already pointed out, the method according to any one of the embodiments of the present invention allows to obtain PHB in an efficient way.

In particular, the method according to any of the embodiments herein described allows to obtain PHB or a salt thereof with a yield of not less than 83% by weight on the weight of the dry cell mass.

Surprisingly, the polyhydroxybutyrate obtained by the method according to any one of the embodiments of the present invention has a high molecular weight, for example between about 7.6 and about 9.2 MDa, more particularly between about 7.8 and about 8.8 MDa even more in particular between about 8 and about 8.5 MDa, and characteristics that make it particularly suitable for the production of articles which must withstand high mechanical stresses such as, for example, soles and/or heels for footwear.

Therefore, the present invention also refers to polyhydroxybutyrate obtained or obtainable by the method according to any of the embodiments herein described, preferably having a molecular weight of between about 7.6 and about 9.2 MDa, more preferably, of between about 7.8 and about 8.8 MDa, even more preferably between about 8 and about 8.5 MDa.

The present invention also relates to an article comprising, or consisting of, PHB obtained or obtainable by the method according to any of the embodiments described herein. Said article is preferably selected from the group comprising, or consisting of: soles and/or heels for footwear, packaging (such as bags, boxes, foams), toys, kitchen utensils (such as plates, cutlery, pot holders), objects (ornaments, covers for phones), medical devices, personal care products (such as razors, toothbrushes, brushes), office items (such as pen holders), and more preferably soles and/or heels for footwear.

Thanks to the good performance of PHB in terms of biocompatibility in human tissue, it could also be used in the medical field, for example, for the controlled release of drugs, surgical sutures, production of heart valves, etc.

The person skilled in the art will understand that although, by way of example, reference has been made to some articles in particular, the most disparate articles comprising, or consisting of, polyhydroxybutyrate according to the present invention can be prepared.

All these articles can be prepared by conventional plastic material molding techniques widely known in the art. However, the inventors of the present invention have also identified an alternative and improved process which can advantageously be used for the production of articles comprising, or consisting of, PHB.

The present invention therefore also refers to a process for the production of an article comprising, or consisting of, PHB which comprises the following steps:
preparing PHB according to the method of any of the embodiments herein described;
compounding by twin-screw extrusion and/or reactive extrusion, preferably by adding one or more excipients to obtain a polymeric matrix;
pre-drying of the polymeric matrix thus obtained at about 80° C. preferably for 5-9 hours;
injection of the dried polymeric matrix into a mold preferably wherein the injection temperature is between about 135 and about 155° C. and/or preferably wherein the mold temperature is between about 25 and about 35° C.

Suitable excipients and/or additives in the context of the present invention are those conventionally known to be used in the injection molding of plastics. By way of non-limiting example, suitable excipients and/or additives can be natural plasticizing agents such as derivatives of vegetable oils preferably selected from the group which comprises, or consists of, epoxidized triglycerides of castor oil, epoxidized soybean oil, cardanol oil, epoxidized linseed oil and mixtures thereof. Furthermore, as excipients and/or additives, fillers such as natural gums or cellulose or its derivatives can also be used, for example generated as by-products from the woodworking industry or agriculture. These natural fillers are inexpensive, non-toxic, they are renewable materials and above all they impart to the material characteristics such as low density, high rigidity, resistance to corrosion while maintaining the biodegradability of the PHB.

The mixture of agri-food wastes of the invention has made it possible to obtain a PHB having mechanical, elastic, and thermal properties comparable to those of plastic materials such as polypropylene or in any case superior to those of PHB obtainable with the processes known to date. By virtue of these properties, the polyhydroxybutyrate of the present invention has proved particularly suitable for the preparation of soles and/or heels for footwear.

As will be evident to those skilled in the art from the examples provided below, the present invention constitutes a more economical and environmentally sustainable alternative to the processes for the production of bioplastics, in particular PHB, known in the art. Advantageously, the PHB obtainable by the method according to any of the embodiments of the present invention has optimal mechanical and elastic performances which make it suitable for the most disparate uses, in particular in the footwear industry with particular reference to the production of biodegradable shoe heels obtained by injection molding of PHB according to the invention.

EXAMPLES

Some non-limiting examples of embodiments according to the present invention are reported below. Modifications or variations of the embodiments exemplified here, obvious to one skilled in the art, are included in the appended claims.

Example 1: Mixture According to the Invention orange zest 15%
wheat bran 10%
rice husk 10%
olive oil vegetation waters and pomace 63%
castor oil epoxidized triglycerides 2%

Said mixture allows to obtain PHB with a yield of not less than 87% by weight on the weight of the dry cell mass. The obtained polyhydroxybutyrate has a high molecular weight, for example between 8.3 and 9.2 MDa.

Example 2: Mixture According to the Invention orange zest 10%
wheat bran 12%
rice husk 13%
olive oil vegetation waters and pomace 62%
soybean oil 3%

Said mixture allows to obtain PHB with a yield of not less than 84% by weight on the weight of the dry cell mass. The obtained polyhydroxybutyrate has a high molecular weight, for example between 8.0 and 8.7 MDa.

The mixtures according to the invention referred to in Examples 1 and 2 were also prepared using a weight ratio between solid food wastes (orange peel, wheat and rice husk) on liquid food wastes (vegetation water and olive oil pomace) equal to 20:80 and 40:60 always guaranteeing a good process yield and a high molecular weight of the PHB obtained.

Example 3: Comparative Mixture orange zest 15%
wheat bran 15%
rice husk 20%
olive oil vegetation waters and pomace 48%
soybean oil 2%

Said comparative mixture shows that when the weight ratio between solid food wastes and liquid food wastes is not 35:65, the PHB has a yield of less than 60% by weight on the weight of the dry cell mass. Furthermore, the obtained polyhydroxybutyrate has a molecular weight lower than 5.3 MDa.

Therefore, with a weight ratio of solid food wastes to liquid food wastes of about 50:50 the PHB is obtained but in a less efficient way and with a molecular weight not as high as it happens for the preferred embodiment according to the invention.

By using weight ratios that do not fall within the range 20:80 -40:60, on the other hand, the process yields are low and the PHB has an insufficient molecular weight.

Example 4: Preparation of Poly-β-Hydroxybutyrate According to the Invention 1-pretreating the solid agri-food wastes with a suitable solvent, preferably distilled water for 2 h at pH 7.0 and 30° C., in order to separate the soluble fraction of said solid food wastes and mix the soluble fraction of said solid food wastes thus obtained with the liquid food waste, wherein the soluble fraction of said solid food wastes is mixed with said liquid food wastes in a weight ratio of 35:65.

2-Incubating *Bacillus megatarium* QM B1551 in CSTR reactor for 10 h at PH 7.0 and 30° C. with an agri-food waste mixture, where the agri-food waste mixture comprises solid agri-food wastes such as orange peel, wheat bran, rice husk and liquid agri-food wastes such as olive oil vegetation water, pomace and at least one plasticizer additive between epoxidized triglycerides of castor oil, epoxidized soybean oil, cardanol oil, epoxidized linseed oil;

3-Incubating *Bacillus megatarium* QM B1551 in a batch reactor with pH of 7.0 and a temperature of 35° C. for 48 h wherein the incubation conditions are adjusted in favor of the carbon source.

4-Recovering the granules contained in the bacterial cells, with cell lysis, followed by the separation of the biopolymer from the rest of the cellular materials.

5-Extracting PHA from biomass at room temperature using halogenated solvents such as chloroform, dichloromethane or 1,2-dichloroethane, and using an anti-solvent (ethanol, methanol or acetone).

6-After immersing the PHA in distilled water (hypotonic medium), centrifuge for 1 h, settle and filter.

7-washing the PHA with detergents (example: SDS) to further purify the polymer.

8-Carry out a further washing, flocculation and drying: the polymer is derived in the form of a white powder which is then melted, extruded and converted into granules according to the traditional technology of petrochemical synthesis polymers.

Example 5: Characterization of the Phb Obtained According to the Invention

The PHB obtained according to the invention is characterized by mechanical values much higher than the PHBs available on the market, in particular it is evident how the elastic modulus, the tensile elongation and the impact resistance with notch, fundamental values for the application of the polymer on products with high mechanical requirements, are significantly higher.

Mechanical values of a standard PHB on the market:

| Property | Standard | Unit | Test conditions | Value |
|---|---|---|---|---|
| Tensile elongation | ISO 527-1-2 | % | v = 50 mm/min | 13 |
| Flexural modulus of elasticity | ISO 178 | MPa | v = 2 mm/min | 1200 |
| Izod bump with notch | ISO 179/1eA | kJ/m$^2$ | 23° C. | 2 |

Mechanical values of a PHB obtained with the formula of Example 1:

| Property | Standard | Unit | Test conditions | Value |
|---|---|---|---|---|
| Tensile elongation | ISO 527-1-2 | % | v = 50 mm/min | 25 |
| Flexural modulus of elasticity | ISO 178 | MPa | v = 2 mm/min | 1600 |
| Izod bump with notch | ISO 179/1eA | kJ/m$^2$ | 23° C. | 15 |

Example 6: Preparation of Sole and/or Heel for Footwear

Polyhydroxybutyrate obtained according to Example 4 is compounded by twin screw extrusion.

After that, the polymer mass is dried at 80° C. for about 5-9 hours and subsequently poured into the injection molding machine set at an operating temperature of 135 -155° C. and flows into the mold, for example a heel mold for footwear, in which the mold temperature is set at 25-35° C. Before removing the item, for example the heel, from the mold it is advisable to wait at least 40-50 seconds otherwise there is a risk of deformation of the same. Finally, the article must be left to rest at room temperature for 48 hours before using it for further processing, for example, before attaching it to a shoe sole. The rest period favors the achievement of an optimal crystalline structure and therefore also of an optimal mechanical resistance.

The invention claimed is:

1. A method for preparing polyhydroxybutyrate (PHB) or a salt thereof, comprising:
    incubating *Bacillus megaterium* QM B1551 in a culture medium comprising a mixture of agri-food wastes, said *Bacillus megaterium* QM B1551 producing polyhydroxybutyrate;
    separating or collecting the polyhydroxybutyrate from the culture medium,
        wherein the mixture of agri-food wastes comprises solid agri-food wastes including orange peels, wheat bran, and rice husks and liquid agri-food wastes including olive oil vegetation waters and pomace, and
        wherein said solid agri-food wastes and liquid agri-food wastes are present in a weight ratio of 35:65, based on the total weight of the mixture,
        wherein said separated or collected polyhydroxybutyrate has a molecular weight between 7.6 and 9.2 MDa, and
        wherein said separated or collected polyhydroxybutyrate is obtained with a yield of not less than 83% by weight based on a dry cell mass weight of the mixture.

2. The method of claim 1, further comprising:
    pre-treating the solid agri-food wastes with hot distilled water to separate a soluble fraction; and
    mixing the soluble fraction thus obtained with said liquid agri-food wastes.

3. The method of claim 1, wherein said molecular weight is between 7.8 and 8.8 MDa.

4. The method of claim 3, wherein said molecular weight is between 8.0 and 8.5 MDa.

* * * * *